United States Patent
Ahn et al.

(10) Patent No.: US 7,713,295 B2
(45) Date of Patent: May 11, 2010

(54) HYPERTENSION DESCENDING DEVICE

(75) Inventors: Moon-Hwi Ahn, Gunsan-si (KR); Sang-Wuk Ahn, Gunsan-si (KR)

(73) Assignee: Acutend, Inc., San Jose, CA (US)

( * ) Notice: Subject to any disclaimer, the term of this patent is extended or adjusted under 35 U.S.C. 154(b) by 6 days.

(21) Appl. No.: 11/271,735

(22) Filed: Nov. 14, 2005

(65) Prior Publication Data
US 2006/0178715 A1 Aug. 10, 2006

Related U.S. Application Data

(63) Continuation of application No. 10/793,891, filed on Mar. 8, 2004, now abandoned.

(30) Foreign Application Priority Data

May 24, 2003 (KR) .................... 10-2003-0033226

(51) Int. Cl.
*A61F 7/00* (2006.01)
(52) U.S. Cl. .................. 607/109; 607/96; 607/108
(58) Field of Classification Search ............. 606/20–26; 607/96, 99; 604/291
See application file for complete search history.

(56) References Cited

U.S. PATENT DOCUMENTS

| | | | | |
|---|---|---|---|---|
| 3,133,539 A | * | 5/1964 | Eidus | 607/96 |
| 3,971,229 A | * | 7/1976 | Privas | 62/3.62 |
| 4,308,013 A | * | 12/1981 | Major | 433/32 |
| 4,640,284 A | * | 2/1987 | Ruderian | 607/96 |
| 5,097,828 A | * | 3/1992 | Deutsch | 607/104 |
| 5,097,829 A | * | 3/1992 | Quisenberry | 607/105 |
| 5,207,674 A | | 5/1993 | Hamilton | |
| 6,017,337 A | * | 1/2000 | Pira | 606/20 |
| 6,023,932 A | | 2/2000 | Johnston | |
| 6,125,636 A | * | 10/2000 | Taylor et al. | 62/3.5 |
| 6,165,206 A | | 12/2000 | Tu | |
| 6,522,926 B1 | * | 2/2003 | Kieval et al. | 607/44 |
| 6,629,417 B2 | * | 10/2003 | Haas et al. | 62/3.2 |
| 6,679,908 B2 | * | 1/2004 | Shimizu | 607/109 |
| 7,037,326 B2 | * | 5/2006 | Lee | 607/108 |
| 2001/0023364 A1 | | 9/2001 | Ahn | |

* cited by examiner

*Primary Examiner*—Roy D Gibson
(74) *Attorney, Agent, or Firm*—Law Offices of Ira D. Blecker, P.C.

(57) ABSTRACT

Disclosed is a hypertension descending device capable of curing a hypertension disease by stimulating a patient's Acupuncture point Renying (or referred to as "carotid sinus") by repeated cold pressure vibration. The hypertension descending device is designed to allow common users to use it easily, and provides a good hypertension descent effect by stimulating the patient's carotid sinus (Acupuncture point Renying) portion while maintaining a uniform cooling temperature of the contact tip, which is in contact with the patient's carotid sinus (Acupuncture point Renying) portion.

18 Claims, 11 Drawing Sheets

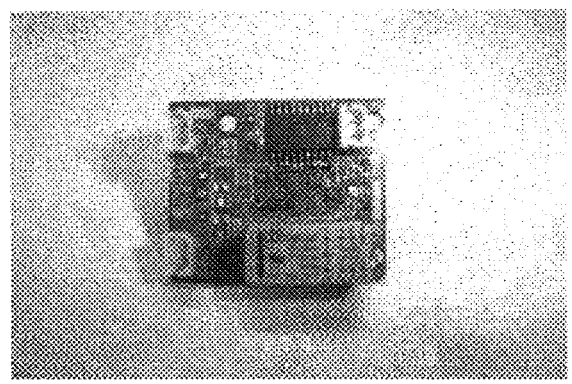
FIG.3A
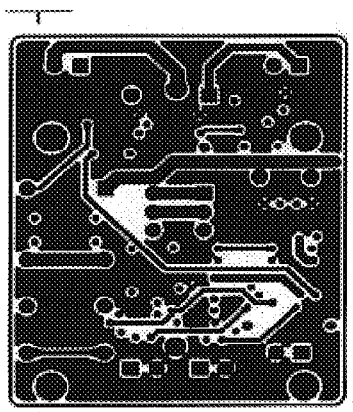 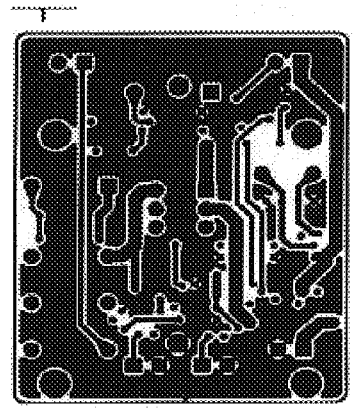
FIG.3B  FIG.3C

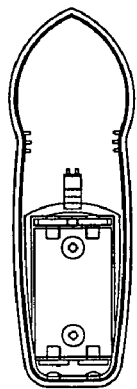 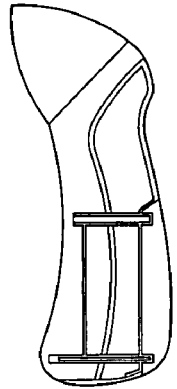 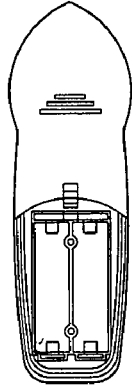
FIG.4A  FIG.4B  FIG.4C
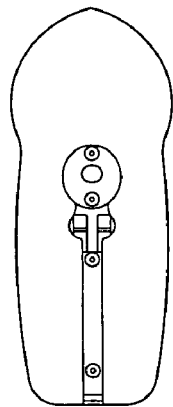 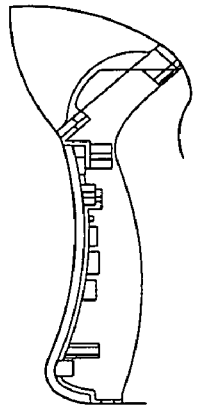 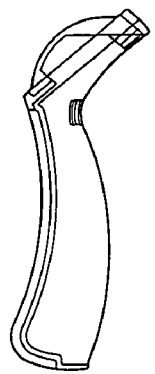
FIG.4D  FIG.4E  FIG.4F

HYPERTENSION DESCENDING DEVICE

This application is a Continuation of application Ser. No. 10/793,891 filed on Mar. 8, 2004 now abandoned, and for which priority is claimed under 35 U.S.C. §120; and this application claims priority of Application No. 2003-0033226 filed in Korea on May 24, 2003 under 35 U.S.C. §119; the entire contents of all are hereby incorporated by reference.

TECHNICAL FIELD

The present invention relates to a hypertension descending device using a cooling device, and more particularly, to a hypertension descending device capable of curing a hypertension disease by stimulating a patient's acupuncture point Renying (or referred to as "carotid sinus") by repeated cold pressure vibration.

BACKGROUND ART

In general, we depend on medicinal therapy, such as use of internal medicines and/or injection, in an aspect of the Western medical science or on acupuncture therapy in an aspect of the Oriental medical science to cure hypertension. However, in case of the medicinal therapy of the Western medical science, such as internal use of antihypertensive agent, it is quite probable that medication gives rise to ill effects as a patient must take medicines almost through his/her life. Meanwhile, the acupuncture therapy of the Oriental medical science requires highly skilled technique and specialization, shows different curing effects little by little whenever the patient is treated, and may cause pain when the patient is treated.

In the Western medical science, the place for curing a hypertension disease is referred to as "carotid sinus", and a physician do a carotid sinus massage with fingers during makeshift measures of the patients related with heart's blood. The carotid sinus massage decreases systolic blood pressure during a short period of time, but can maintain the descended blood pressure only for several minutes.

The inventor of the present invention made a clinical test to a patients' meridian points, and as a result of the clinical test, it was confirmed that the hypertensive patient's blood pressure was descended and returned to normal blood pressure when low-temperature stimulation was applied to the "acupuncture point Renying (ST 9 acupoint)", which was classified in the Oriental medical science, located at the left side or right side (carotid sinus) of the patient's neck part for a predetermined period of time. Also, it was confirmed that a headache and fever were cured when low-temperature stimulation was applied to the other Spots on the body suitable for acupuncture (i.e. the acupuncture point Hegu, the acupuncture point Quchi, the acupuncture point Taiyang, the acupuncture point Fengchi, the acupuncture point Baihui, the acupuncture point Zusanli, the acupuncture point Taichong, the acupuncture point Yongquan, the acupuncture point Renzhong, the acupuncture point Dazhui, the acupuncture point Tongtian).

Therefore, an object of the present invention is to provide a device capable of curing hypertension by stimulating the patient's carotid sinus (acupuncture point Renying) by repeated cold pressure vibration in person with no ill effects.

To achieve the above object, a cooling device is in contact with the patient's carotid sinus (acupuncture point Renying) and stimulates it at a low temperature of −1° C.~+5° C. for about 4~10 minutes. The contact tip of the present invention maintains a temperature of −15° C.~+5° C. in case it does not contact a human's body.

FIG. 1 shows a product invented by the inventor of the present invention. In the drawing, a heat sink made of metal material with a good heat conductivity includes a conical cooling pin having a number of miniaturized vibration motors arranged at regular intervals to emit heat to the outside easily, and a coupling slit formed in the front end thereof to couple a cap, and through holes formed in the side surface to draw out electric wires.

A thermo electric module (thermoelement) is mounted at the center of the upper end portion of the heat sink, and at this time, a heat generating surface of the thermo electric module is directed to the heat sink, and a cooling surface of the thermo electric module (hereinafter, called "T.E module") has a contact tip, which has a hemispheric magnet mounted at the top of the T.E module. Furthermore, the electric wires of the T.E module are drawn out of the lower end of the heat sink through the holes formed in the side surface of the heat sink.

The contact tip has the optimal volume to transmit cooling temperature, which is set by a user, to the patient's affected portion the fastest.

A cooling fan is mounted at the lower end portion of the heat sink to effectively remove heat emitted from the heat generating surface of the T.E module, thereby maximizing a cooling efficiency of the T.E module.

DISCLOSURE OF INVENTION

Accordingly, the present invention has been made in view of the above problems, and it is an object of the present invention to provide a hypertension descending device capable of stimulating a patient's carotid sinus (acupuncture point Renying) at a low temperature, which includes a temperature sensor for sensing a cooling temperature of a contact tip contacting with the patient's carotid sinus (Acupuncture point Renying), and which compares a temperature of the contact tip set by a user with a temperature of the contact tip sensed by the temperature sensor to automatically control the temperature of the contact tip according to the temperature difference, thereby automatically setting the cooling temperature of the contact tip according to the patients' physical constitutions.

Another object of the present invention is to provide a hypertension descending device capable of stimulating a patient's carotid sinus (Acupuncture point Renying) at a low temperature, which includes a heat sink and a cooling fan mounted at the lower portion of a Thermo electric module (hereinafter, called "T.E module") for cooling down the contact tip substantially, thereby improving cooling efficiency of the T.E module.

To achieve the above objects, the contact tip protrudes to the upper end portion of a case to be in contact with the patient's carotid sinus (Acupuncture point Renying) portion, and the T.E module is disposed on the lower end of the contact tip to cool down the temperature of the contact tip to the temperature set by the user.

BRIEF DESCRIPTION OF DRAWINGS

Further objects and advantages of the invention can be more fully understood from the following detailed description taken in conjunction with the accompanying drawings in which:

FIG. 3 is a view of a structure and a circuit diagram of a controlling device;

FIG. 4 is a view showing designs of the outward pattern of the hypertension descending device;

BEST MODE FOR CARRYING OUT THE INVENTION

The present invention will now be described in detail in connection with preferred embodiments with reference to the accompanying drawings.

Figure 6A:
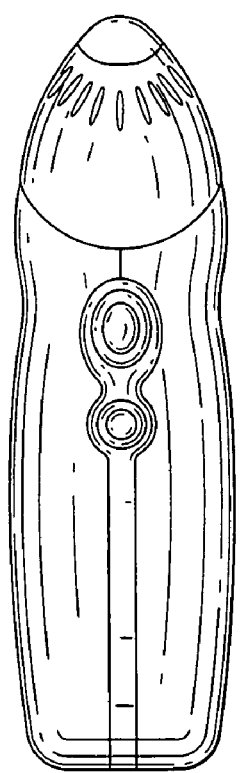
FIG. 6 is a view showing the outward pattern of the hypertension descending device.
Figure 6B:

FIG. 6 shows a case, which is the outward appearance of a hypertension descending device using low temperature according to the present invention. A contact tip to be in contact with a patent's carotid sinus (Acupuncture point Renying) portion protrudes upwardly from the upper end portion of the case.

Figure 1:
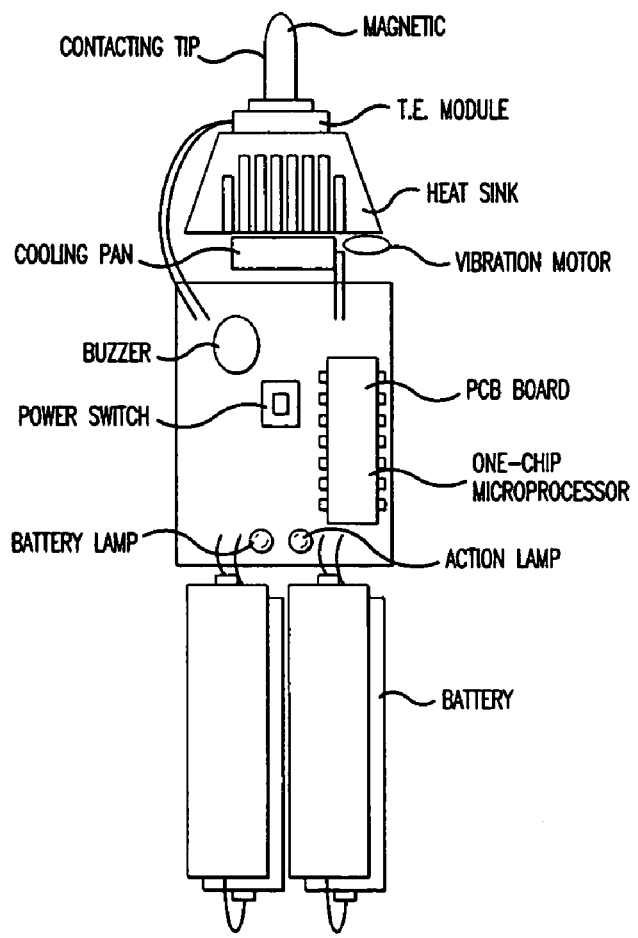
FIG. 1 is a sectional view of a structure of a cooling device according to the present invention.
Figure 2:
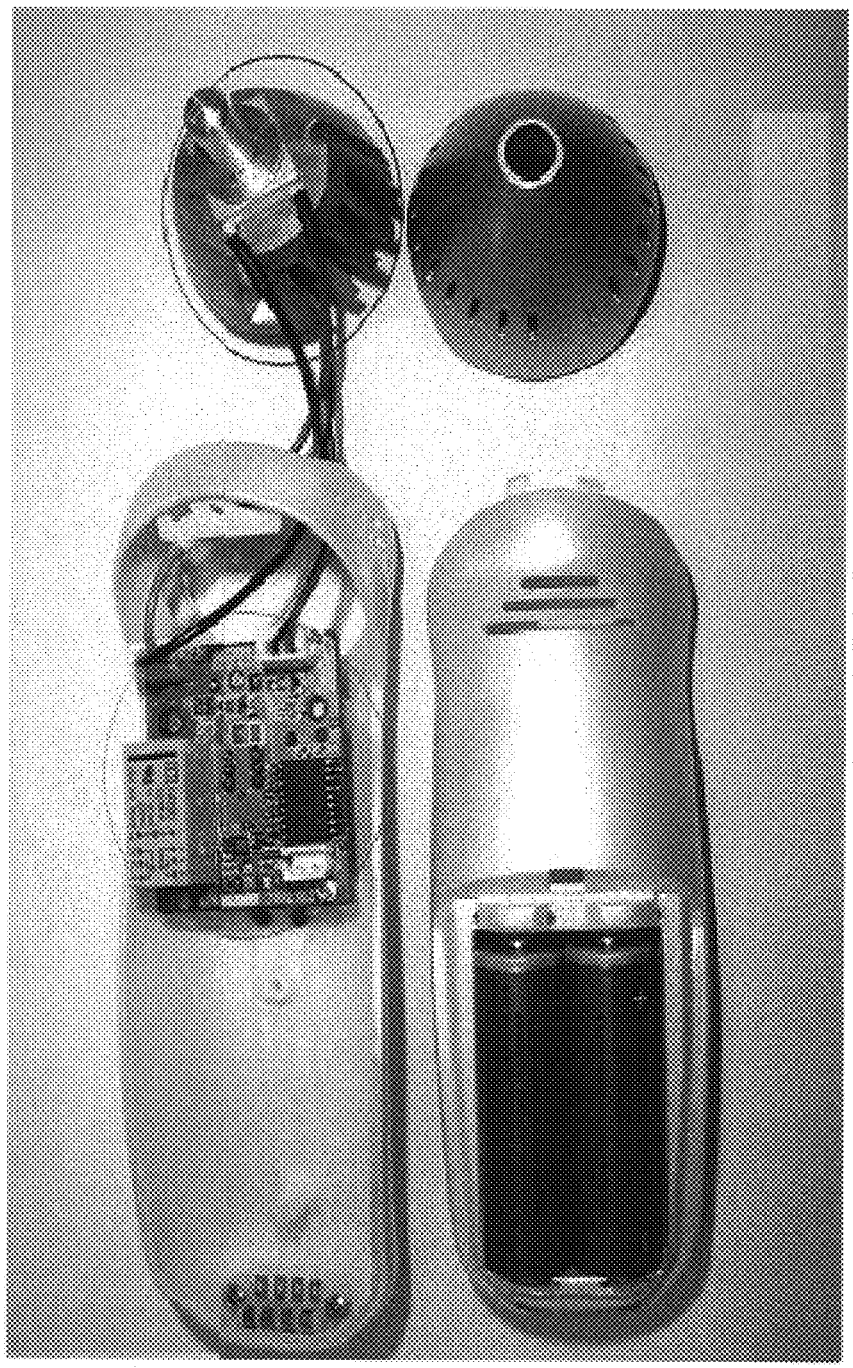
FIG. 2 is a photograph of a hypertension descending device according to the present invention.

As shown in FIG. 2, a thermo electric module (hereinafter, called "T.E module") is mounted at the lower end portion of the contact tip to cool the contact tip to a cooling temperature set by the user according to input current. At this time, as shown in FIG. 1, the T.E module has a cooling surface formed on the upper surface thereof, which is in contact with the contact tip, and a heat generating surface formed on the lower surface thereof, which is in contact with a heat sink.

The heat sink is mounted on the lower portion of the T.E module, and has a cooling fan mounted at the lower end thereof for discharging heat emitted from the heat sink to the outside so as to improve a cooling efficiency of the T.E module.

Therefore, when the T.E module is operated, the cooling fan is also operated, and then, a great deal of heat is removed fast through the heat sink being in contact with the heat generating surface of the T.E module using forced convection, so that the T.E module shows more improved cooling efficiency.

Meanwhile, the present invention includes a controlling device for maintaining the cooling temperature of the contact tip set by the user. The controlling device includes a key input part (switch) for starting and terminating operation, an LED for displaying the present status, and a buzzer for informing start and termination of operation to the user.

The operation of the present invention having the controlling device (see FIG. 5) will be described as follows.

First, when a user supplies power source by manipulating the key input part, the buzzer informs the user of start of operation by a continuous sound of "buzz~, buzz~", and the LED emits light to show application of power source. The controlling device controls strength of electric current supplied to the T.E module according to supplied control signal, and the T.E module cools the contact tip according to the electric current supplied from the controlling device.

At this time, a temperature sensor mounted on the contact tip senses the present cooling temperature of the contact tip and transmits it to a temperature controller, and the temperature controller compares the present cooling temperature sensed by the temperature sensor with the temperature of the contact tip set by the user. After that, the temperature controller outputs control signal, which is modulated in pulse width corresponding to the temperature difference between the set temperature and the present cooling temperature, to a current controller. The current controller controls the strength of electric current supplied to the T.E module according to the pulse width modulated control signal inputted from the temperature controller, so that the cooling temperature of the contact tip can be maintained at the cooling temperature set by the user.

Furthermore, when the T.E module is operated, the cooling fan is also operated, and smoothly emits heat emitted from the heat generating surface of the T.E module through the heat sink to improve the cooling efficiency of the T.E module, so that the contact tip can reach a desired cooling temperature faster.

Figure 5:
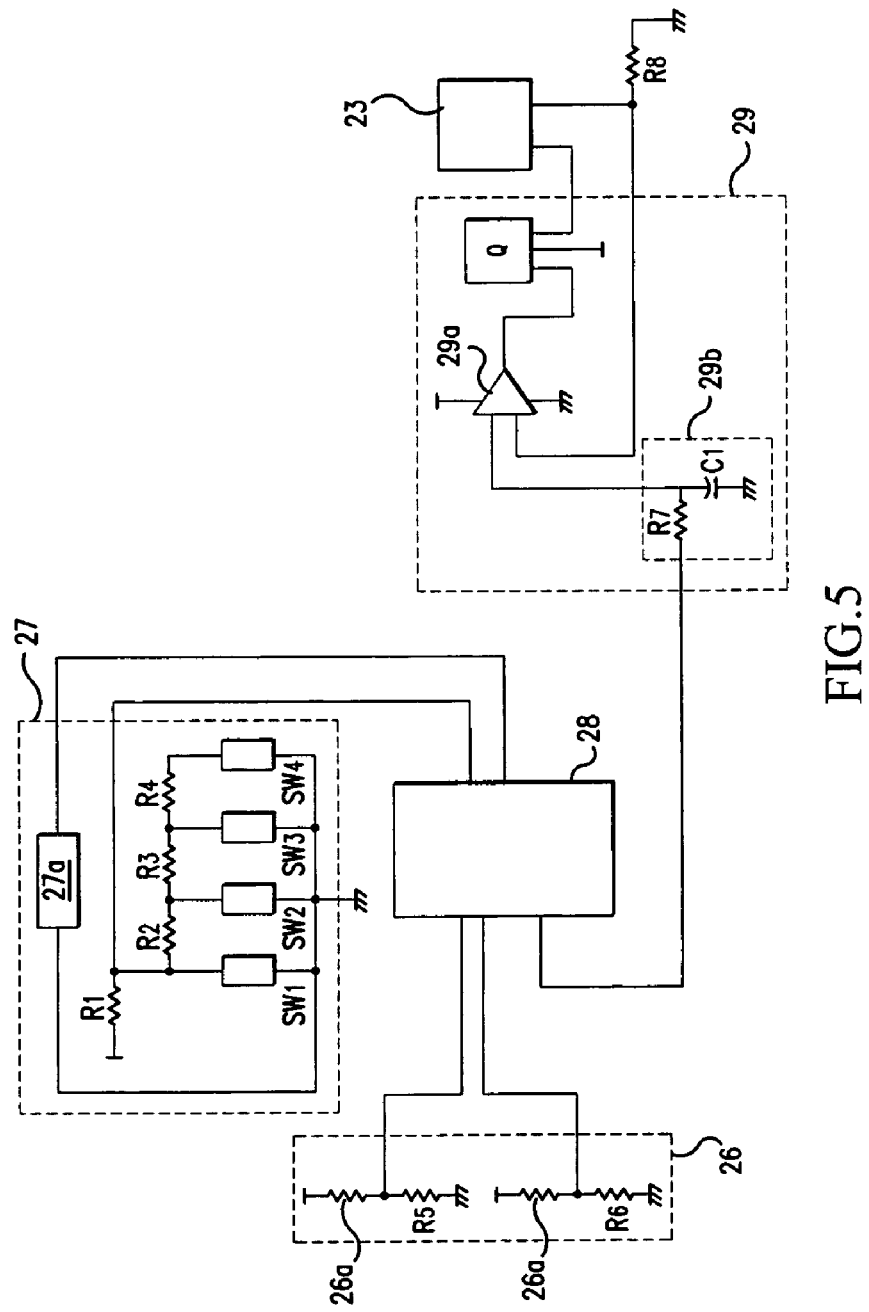
FIG. 5 is a circuit diagram of the hypertension descending device.

Meanwhile, FIG. 5 is a simple circuit diagram showing the controlling device applied to the present invention.

In the drawing, the temperature sensor 26 includes a thermister 26a and resistances R5 and R6, which have resistance values varied according to a temperature change of the surroundings.

Therefore, when the temperature of the contact tip is changed, the temperature controller 28 can sense the present cooling temperature of the contact tip while the resistance value of the thermister 26a is varied.

The key input part 27 includes a number of switches SW1~SW4 and resistances R1~R4 for allowing the user to input a desired setting temperature. In the drawings, unexplained reference numeral 27a is a buzzer.

The current controller 29 is to control electric current supplied to the T.E module 23 according to the pulse width modulated control signal, which is outputted from the temperature controller 28. The current controller 29 includes a smoothing filter 29b, which has resistances R7 and R9 and a capacitor C1, and which converts the pulse width modulated control signal outputted from the temperature controller 28 into DC signal of a predetermined level, and a transistor Q for varying strength of electric current supplied to the T.E module 23 according to signal outputted from an arithmetic amplifier 29a.

That is, the current controller 29 receives the control signal, which is supplied from the temperature controller 28, from the smoothing filter 29b, and converts it into DC signal of the predetermined level. The DC signal of the predetermined level outputted from the smoothing filter 29b is supplied to the transistor Q after being amplified in the arithmetic amplifier 29a. The transistor Q supplies electric current corresponding to inputted voltage to the T.E module, so that the cooling operation of the T.E module 23 can be realized.

The level of DC signal outputted from the smoothing filter 29b is varied according to pulse width of control signal outputted from the temperature controller 28, and the strength of electric current supplied to the T.E module 23 is varied according to the level of DC signal outputted from the smoothing filter 29b, so that the cooling temperature of the contact tip can be controlled.

Figure 7:
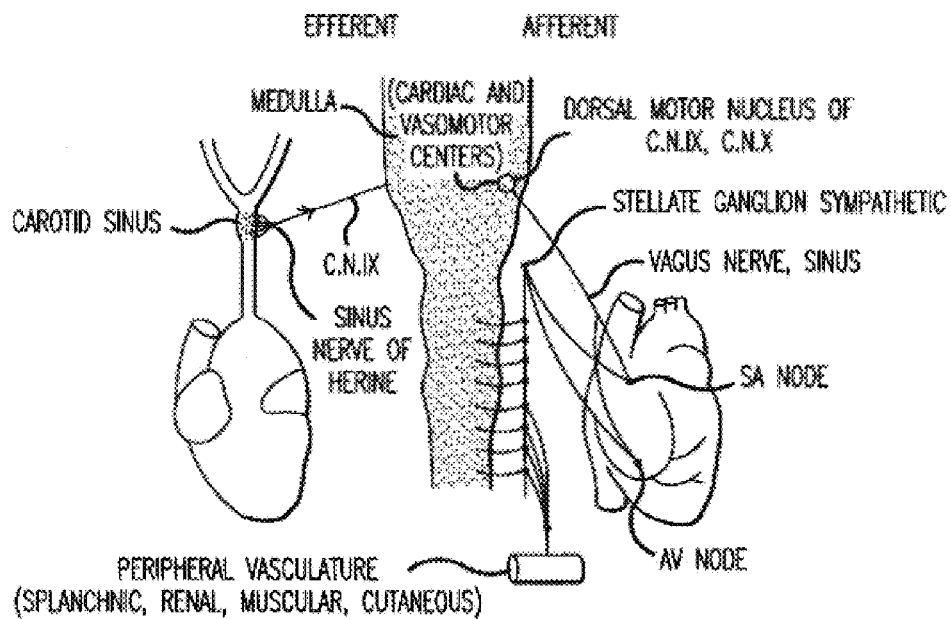
FIG. 7 is a view of an anatomized structure of a human's carotid sinus.
Figure 8:
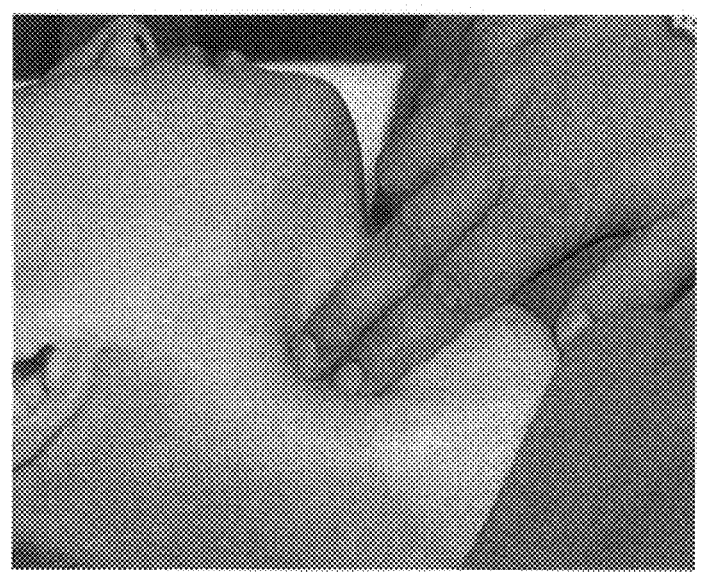
FIG. 8 is a view of the position of a human's carotid sinus.
Figure 9:
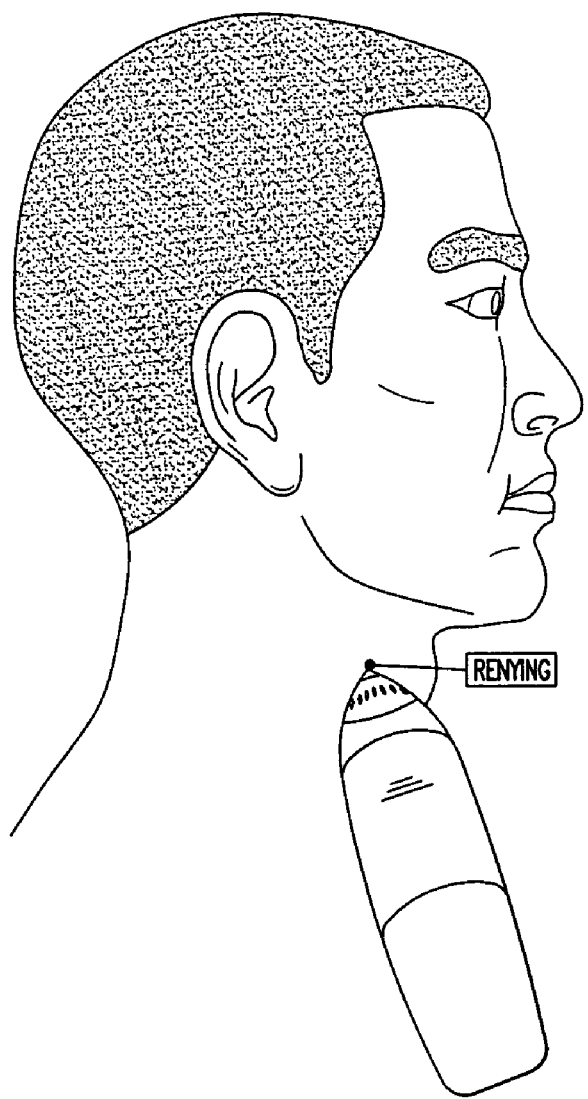
FIG. 9 is a view of the position of a human's Acupuncture point Renying, showing a state in which the hypertension descending device is in contact with the Acupuncture point Renying.
Figure 10:
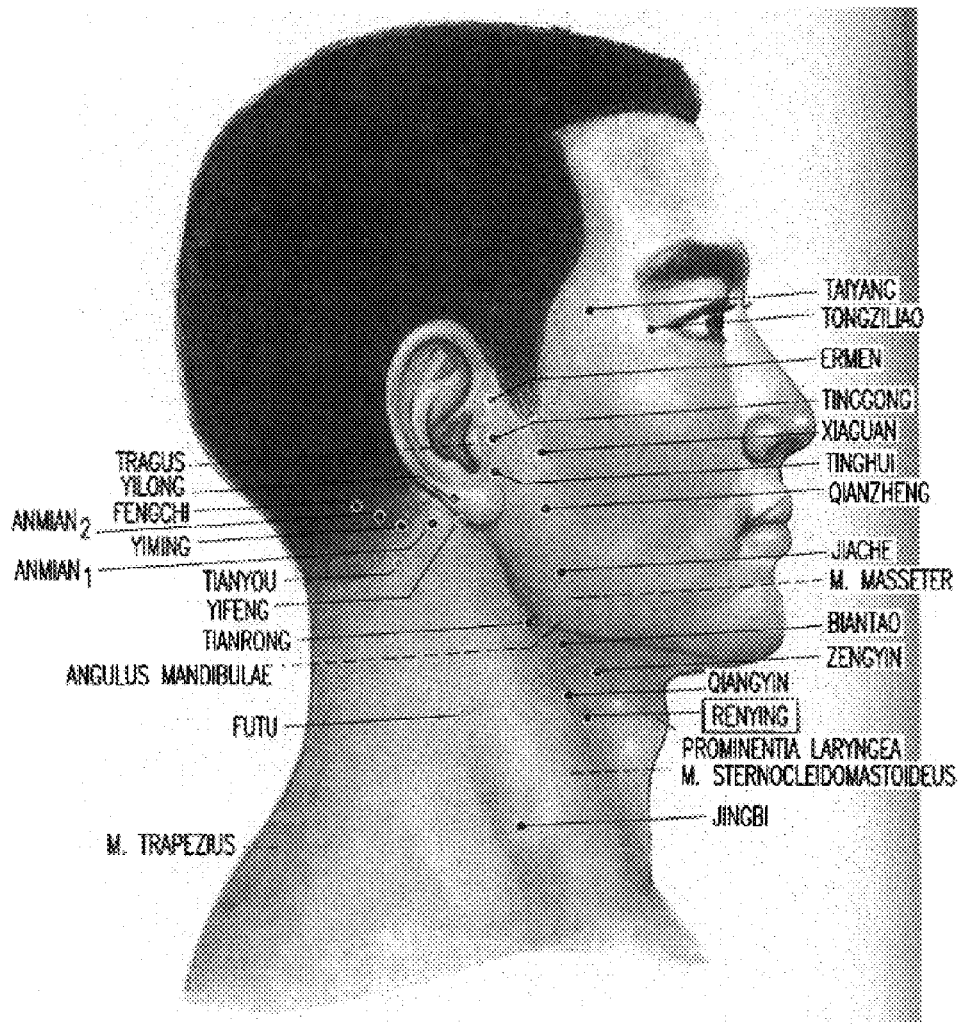
FIG. 10 is a view of the position of a human's Spots on the body suitable for acupuncture.
Figure 11:
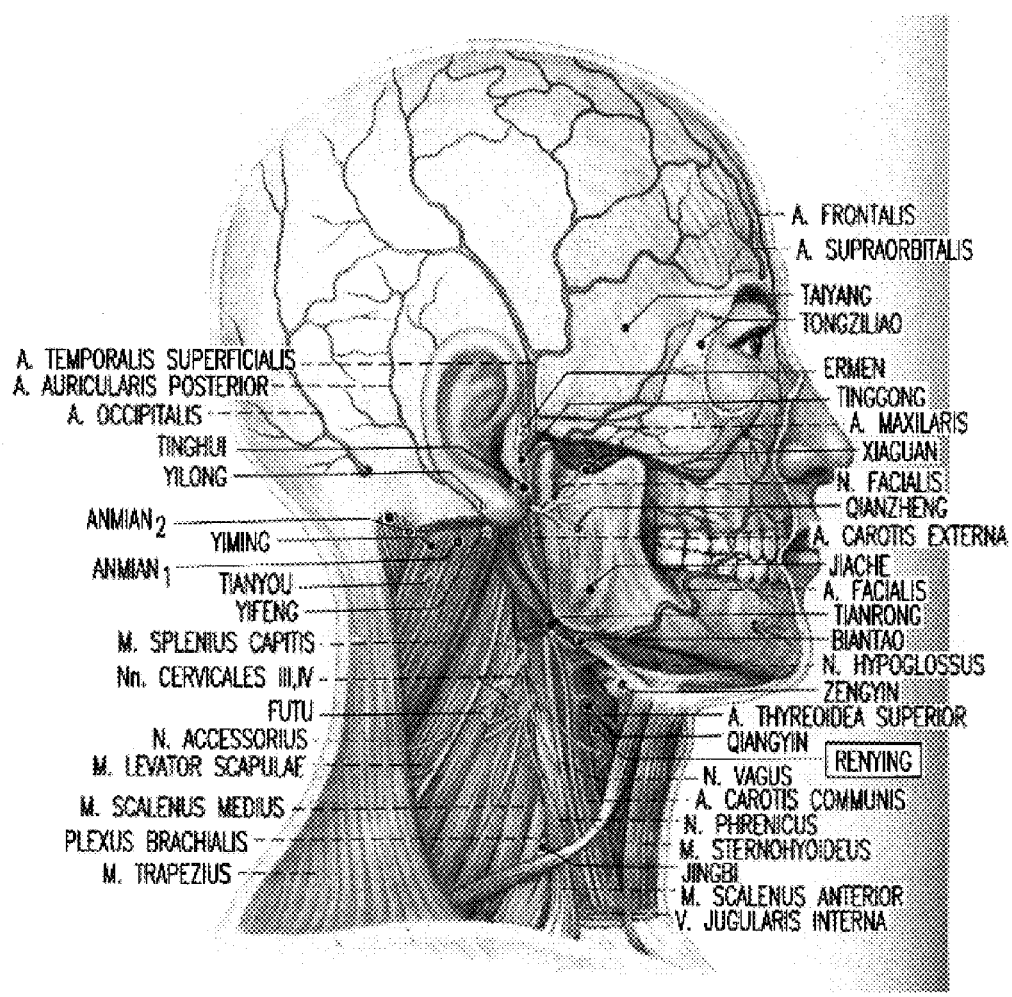
FIG. 11 is a view of the anatomical chart showing a human's Spots on the body suitable for acupuncture.
Figure 12:
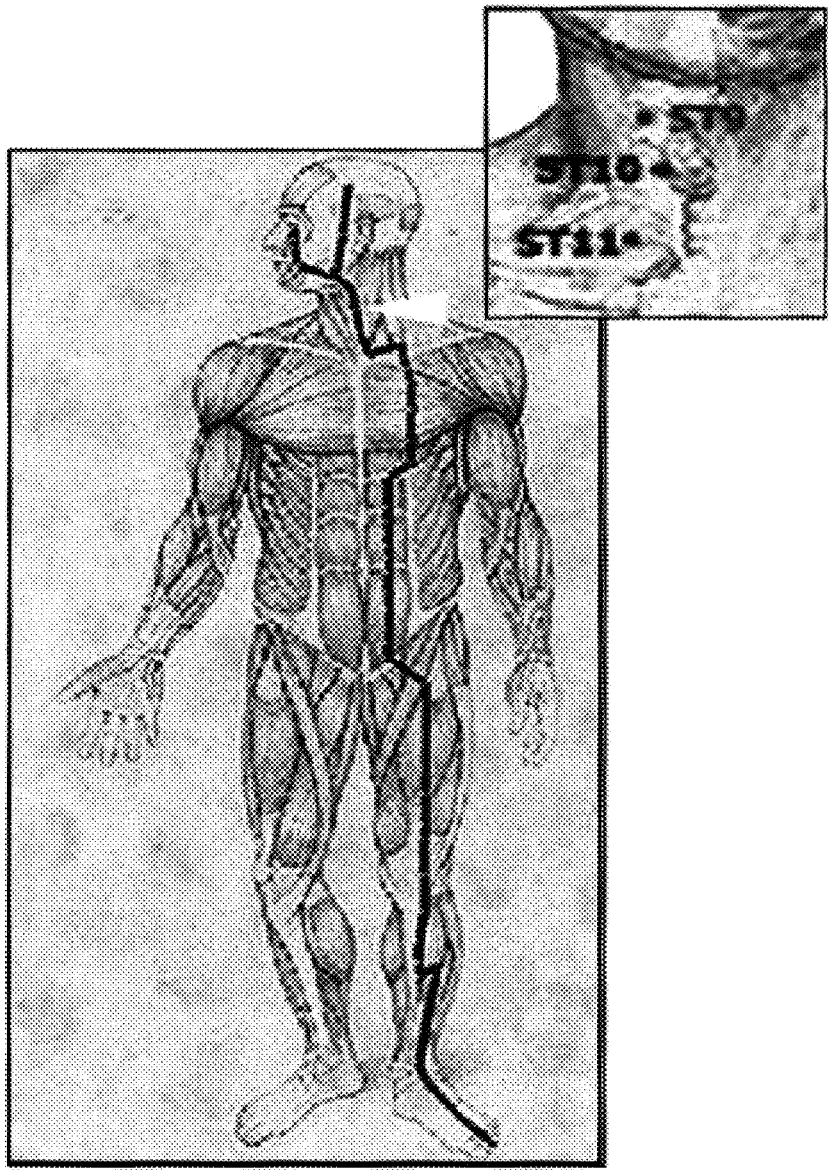
FIG. 12 is a view of the position of a human's Acupuncture point Renying (ST 9 acupoint).

As described above, after the operation is started, when the user contacts the cooled contact tip onto the patient's carotid sinus (Acupuncture point Renying) shown in FIGS. 7, 8 and 9 for 4~10 minutes, hypertension can be descended effectively.

As a result of stimulating the patient's carotid sinus (Acupuncture point Renying) portion with cold pressure using the present invention, the numerical value of hypertension was lowered, for example, 60 patients, who had blood pressure of about 170 mmHg, were stimulated at a low temperature of about 2° C.±3° C. for 4~10 minutes every day for about 3 months, and thereby, the blood pressure of the hypertensive patients was descended to about 40 mmHg. At this time, duration time of hypertension descending was about 6~8 hours.

As described above, it was confirmed that the cooling temperature was harmless to the human body as the cooling temperature was descended by the human body's temperature, namely, body temperature, even though the low-temperature stimulation was applied to the patient's carotid sinus (Acupuncture point Renying) portion.

Experimental Example

I. Subject and Method of Study

1. Subject

To observe a hypertension descending effect of the hypertension descending device according to the present invention, 120 hypertensive patients, who live in Seosan from October to December of 2002 year, were divided into an HDD group and a control group without regard to age and sex distinction. The HDD group, which used the hypertension descending device, had 60 members, and the control group, which used antihypertensive agent, also had 60 members.

The members of the HDD group and the control group were selected on the basis of patients who were in similar age and disease condition and the same sex distinction. Moreover, the patients, who participated in this experimental test, were all adults and had blood pressure exceeding normal range, which was measured three times within a predetermined period of time.

2. Measuring Method

The HDD group did not take antihypertensive agent at all during the experimental duration, and used only the hypertension descending device according to the present invention. The contact tip of the hypertension descending device was in contact with the patient's Acupuncture point Renying located at the left side or the right side of the human body's neck portion.

The experimental duration was about 3 months by 5 minutes every day, and during the above duration, blood pressure was measured before medical cure, directly after the medical cure, and after 30 minutes from the medical cure.

The control group took antihypertensive agent according to a physician's prescription. The experimental duration was about 3 months, and blood pressure was measured once every day.

To measure blood pressure, an automatic blood pressure measuring device manufactured by the JAWON Medical Co., Ltd. was used.

3. Search Method

To select the HDD group and the control group, the standard (see Table 1) defined by JNC-VI(1997) and WHO/ISH (1999) was applied, and persons who had blood pressure exceeding the normal range were prescribed as hypertensive patients.

During the experimental duration, the members of the HDD group did not take antihypertensive agent at all, and used only the hypertension descending device manufactured by the JAWON Medical Co., Ltd. On the other side, the members of the control group took antihypertensive agent.

TABLE 1

Standard of hypertension defined by JNC-VI(1997) and WHO/ISH(1999)

| Division | Systolic state (mmHg) | Atonic state (mmHg) |
|---|---|---|
| Optimal | <120 | <80 |
| Normal | <130 | <85 |
| High normal | 130-139 | 85-89 |
| Hypertension | | |
| Grade 1 (light case) | 140-159 | 90-99 |
| Borderline hypertension | 140-149 | 90-94 |
| Grade 2 (middle case) | 160-179 | 100-109 |
| Grade 3 (serious case) | >180 | >110 |
| Isolated systolic hypertension | >140 | <90 |
| Borderline | 140-149 | <90 |

4. Criterion of Curing Result

A criterion of curing effect was divided into three stages according to the descending level of systolic blood pressure, and the curing effect was judged by percentage using an Excel program by the Microsoft corporation.

A. Excellent: in case of that systolic blood pressure more than 20 mmHg was descended.

B. Good: in case of that systolic blood pressure of about 10~20 mmHg was descended.

C. Poor: in case of that systolic blood pressure of about 10 mmHg or less was descended.

II. Result

1. Age and Sex Distinction of HDD Group

The subject members for study were all 120 people, including the HDD group having 60 members and the control group having 60 members. The HDD group had 25 males and 35 females, and its average age was 58.9 (see Table 2).

TABLE 2

Distribution of Age in HDD and Control Group

| Age | Male N. | Female N. | Total |
|---|---|---|---|
| 40-49 | 5 | 5 | 10 |
| 50-59 | 7 | 14 | 21 |
| 60-69 | 12 | 16 | 28 |
| 70-79 | 1 | 0 | 1 |
| Total | 25 | 35 | 60 |

N: Number of patient

2. Age and Sex Distinction of Control Group

The control group had 60 members including 28 males and 32 females, and its average age was 58.2 (see Table 3).

TABLE 3

Distribution of Sex in HDD and Control Group

| Age | Male N. | Female N. | Total |
|---|---|---|---|
| 40-49 | 2 | 4 | 6 |
| 50-59 | 14 | 16 | 30 |
| 60-69 | 12 | 12 | 24 |
| 70-79 | 0 | 0 | 0 |
| Total | 28 | 32 | 60 |

3. Grade Distribution of Subject Patient

The 60 members of the HDD group were classified into 18 persons of hypertension grade 1, 37 persons of hypertension grade 2, and 5 persons of hypertension grade 3. The 60 members of the control group were classified into 18 persons of hypertension grade 1, 32 persons of hypertension grade 2, and 10 persons of hypertension grade 3 (see Table 4).

TABLE 4

Grade Distribution of Hypertention

|  | HDD | Control Group | Total |
|---|---|---|---|
| Hypertention Grade 1 | 18 | 18 | 36 |
| Hypertention Grade 2 | 37 | 32 | 69 |
| Hypertention Grade 3 | 5 | 10 | 15 |
| Total | 60 | 60 | 120 |

4. Curing Effect of Hypertension Grades 1 and 2

In the HDD group, the hypertensive patients of hypertension grades 1 and 2 were total 55 persons, wherein 25 persons (45.5%) obtained an excellent curing effect, 23 persons (41.8%) obtained a good curing effect, and so, total 48 persons (87.3%) obtained an effective curing result, but only 7 persons (12.7%) obtained a poor curing result.

Meanwhile, in the control group, the hypertensive patients of hypertension grades 1 and 2 were total 50 persons, wherein 23 persons (46.0%) obtained an excellent curing effect after taking antihypertensive agent, 21 persons (42.2%) obtained a good curing effect, and so, total 44 persons (88.0%) obtained an effective curing result, but only 6 persons (12.0%) obtained a poor curing result (see Table 5).

In case of the hypertension grades 1 and 2, there was little difference between the HDD group and the control group.

TABLE 5

Result in hypertention grade 1 and 2

|  | HDD | Control Group |
|---|---|---|
| Excellent | 25(45.5%) | 23(46.0%) |
| Good | 23(41.8%) | 21(42.0%) |
| Poor | 7(12.7%) | 6(12.0%) |
| Total | 55 | 50 |
| Effect | 48/55(87.3%) | 44/50(88.0%) |

5. Curing Effect of Hypertension Grade 3

There were 5 hypertensive patients of hypertension grade 3 in the HDD group, wherein the 5 hypertensive patients of hypertension grade 3 obtained little curing effect by the hypertension descending device as blood pressure descending of the 5 hypertensive patients was about 10 mmHg or less.

There were 10 hypertensive patients of hypertension grade 3 in the control group, wherein 7 persons (70%) of the hypertensive patients obtained an excellent curing effect after taking antihypertensive agent, and 3 persons (30%) obtained a poor curing effect (see Table 6).

TABLE 6

Result in Hypertention Grade 3

|  | HDD | Control Group |
|---|---|---|
| Excellent | 0(0%) | 7(70%) |
| Good | 0(0%) | 0(0%) |
| Poor | 5(100%) | 3(30%) |
| Total | 5 | 10 |

6. Comparison of Curing Effect 48 persons (80.0%) of the total 60 hypertensive patients in the HDD group obtained an effective curing result using the hypertension descending device according to the present invention, but 51 persons (85.0%) in the control group obtained the effective curing result after taking hypertensive agent (see Table 7).

TABLE 7

Comparison of Effect between HDD and Control Group

|  | HDD | Control Group |
|---|---|---|
| Effect | 48/60(80.0%) | 51/60(85.0%) |

III. Conclusion

To check a hypertension descending effect of the hypertension descending device according to the present invention, the hypertension descending device applied cold stimulation to the Acupuncture point Renying in relation with 120 hypertensive patients of hypertension grades 1, 2 and 3.

1. 87.3% of the hypertensive patients of hypertension grades 1 and 2 in the HDD group obtained the effective curing result by the hypertension descending device according to the present invention, and 88.0% of the hypertensive patients of hypertension grades 1 and 2 in the control group obtained the effective curing result after taking antihypertensive agent, and so, the HDD group and the control group showed similar curing effect.

2. The curing effect of the hypertensive patients of hypertension grade 3 in the HDD group was still less than that of the hypertensive patients of hypertension grade 3 in the control group.

3. The effective curing result of the total hypertensive patients in the HDD group was 80.0%, but that of the total hypertensive patients in the control group was 85.0%.

As you can see from the above, the hypertension descending effect of the hypertension descending device by the low-temperature stimulating device onto the patient's Acupuncture point Renying, and so, it can be used as substitution for antihypertensive agent for the hypertensive patients of hypertension grades 1 and 2, and help to prevent the progress from the hypertension grade 1 to the hypertension grade 2 or 3.

As described above, the hypertension descending device according to the present invention shows excellent effect in hypertension descent. A hypertensive patient of a light case can make a living only by using the hypertension descending device without taking antihypertensive agent. In addition, a hypertensive patient of a serious case can use the hypertension descending device and antihypertensive agent together. In this case, a use amount of antihypertensive agent can be largely reduced.

INDUSTRIAL APPLICABILITY

As described above, the hypertension descending device according to the present invention is designed to allow common users to use it easily, and provides a good hypertension descent effect by stimulating the patient's carotid sinus (Acupuncture point Renying) portion while maintaining a uniform cooling temperature of the contact tip, which is in contact with the patient's carotid sinus (Acupuncture point Renying) portion.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention

What is claimed is:

1. A method of lowering hypertension, comprising:
   providing a source of cold;
   providing a tip in communication with said cold source to form a cooling tip;
   applying said tip externally to the skin at the carotid sinus (Renying point) at the neck of a patient under pressure; and
   said tip stimulating the central nervous system of said patient to lower blood pressure.

2. The method of lowering hypertension according to claim 1, wherein the temperature of said tip is set to about $-2°$ C.$+/-3°$ C. and further comprising the steps of sensing an actual temperature of said tip and comparing the temperature of the tip set to about $-2°$ C.$+/-3°$ C. with an actual temperature of the tip sensed in the step of sensing to automatically control the temperature of the tip.

3. The method of lowering hypertension according to claim 1, wherein the tip is applied for about 4 to 10 minutes.

4. The method of lowering hypertension according to claim 1, further comprising providing a source of vibration in communication with said tip so that said tip is applied with cold and vibration.

5. A method of lowering hypertension comprising:
   obtaining a hypertension lowering device comprising:
      a case;
      a cooling tip mounted on said case and protruding outwardly;
      a thermoelectric module in contact with a lower end of said tip causing said tip to be cooled;
      a heat sink mounted on said thermoelectric module; and
      a cooling fan for providing cooling air to said heat sink; and
   applying cold under pressure through the cooling tip externally to the skin at the carotid sinus (Renying point) at the neck in order to stimulate the central nervous system and lower blood pressure.

6. The method according to claim 5, wherein said case contains a temperature sensor;
   a temperature controller for controlling the cooling temperature of the tip in response to a change in temperature of the contact tip as sensed by said temperature sensor;
   a temperature selection device including switches and resistors for selecting a desired temperature; and
   a current controller for controlling current supplied to said thermoelectric module.

7. The method according to claim 5, wherein the hypertension lowering device further comprising a buzzer for indicating operation of the device.

8. The method according to claim 5, wherein the hypertension lowering device further comprising an LED for indicating operation of the device.

9. The method according to claim 6, wherein an output of said temperature controller is a pulse width modulated control signal.

10. The method according to claim 6, wherein the current controller includes a smoothing filter and a transistor, the smoothing filter having resistors and a capacitor.

11. The method according to claim 10, wherein the transistor varies the strength of electric current supplied to the thermoelectric module according to a signal outputted from an arithmetic amplifier.

12. The method according to claim 5, wherein the hypertension lowering device further comprising an electrical supply.

13. The method according to claim 12, wherein the hypertension lowering device further comprising a power switch for selectively connecting said electrical supply to said thermoelectric module and said cooling fan.

14. The method according to claim 5, wherein said tip is set to a temperature of about $-2°$ C.$\pm3°$ C. and further comprising the steps of sensing an actual temperature of said tip and comparing the temperature of the tip set to about $-2°$ C.$+/-3°$ C. with an actual temperature of the tip sensed in the step of sensing to automatically control the temperature of the tip.

15. The method according to claim 14, wherein the stimulation continues for about 4 to 10 minutes.

16. The method according to claim 15, wherein the hypertension lowering device further comprising at least one vibration motor causing said tip to vibrate so that said tip applies cold and vibration.

17. A method of lowering hypertension, comprising:
   obtaining a hypertension lowering device comprising:
      a case;
      a cooling tip mounted on said case and protruding outwardly;
      a thermoelectric module in contact with said tip causing said tip to be cooled; and
      a heat sink mounted on said thermoelectric module; and
   applying cold under pressure through the cooling tip externally to the skin at the carotid sinus (Renying point) at the neck in order to stimulate the central nervous system and lower blood pressure.

18. The method according to claim 17, wherein said case contains a temperature sensor;
   a temperature controller for controlling the cooling temperature of the contact tip in response to a change in temperature of the contact tip as sensed by said temperature sensor;
   a temperature selection device including switches and resistors for selecting a desired temperature; and
   a current controller for controlling current supplied to said thermoelectric module.

* * * * *